United States Patent
Tsukada

(10) Patent No.: US 9,146,214 B2
(45) Date of Patent: Sep. 29, 2015

(54) LEAKAGE MAGNETIC FLUX FLAW INSPECTION METHOD AND DEVICE

(75) Inventor: Keiji Tsukada, Okayama (JP)

(73) Assignee: National University Corporation Okayama University, Okayama (JP)

( * ) Notice: Subject to any disclaimer, the term of this patent is extended or adjusted under 35 U.S.C. 154(b) by 850 days.

(21) Appl. No.: 13/381,347

(22) PCT Filed: May 28, 2010

(86) PCT No.: PCT/JP2010/059102
§ 371 (c)(1),
(2), (4) Date: Dec. 28, 2011

(87) PCT Pub. No.: WO2011/001771
PCT Pub. Date: Jan. 6, 2011

(65) Prior Publication Data
US 2012/0109565 A1    May 3, 2012

(30) Foreign Application Priority Data

Jul. 1, 2009    (JP) ................................ 2009-157126

(51) Int. Cl.
*G01R 35/00* (2006.01)
*G01N 27/83* (2006.01)

(52) U.S. Cl.
CPC ...................................... *G01N 27/83* (2013.01)

(58) Field of Classification Search
CPC .... G01N 27/83; G01N 27/82; G01N 27/9046
USPC ........................................................ 702/106
See application file for complete search history.

(56) References Cited

U.S. PATENT DOCUMENTS

| 5,245,279 A | * | 9/1993 | Bendzsak ...................... 324/225 |
| 5,614,825 A | * | 3/1997 | Maxfield et al. ............... 324/242 |

(Continued)

FOREIGN PATENT DOCUMENTS

| JP | 63-129862 U | 8/1988 |
| JP | 02-228552 A | 9/1990 |

(Continued)

OTHER PUBLICATIONS

English language translation of Yuji Goto, "The inspection method of the defect using nonlinear eddy current analysis," Journal of the Institute of Electrical Engineers of Japan, vol. 127, No. 11, 2007, pp. 727-730.

(Continued)

*Primary Examiner* — Janet Suglo
*Assistant Examiner* — Stephanie Bloss
(74) *Attorney, Agent, or Firm* — Sterne, Kessler, Goldstein & Fox P.L.L.C.

(57) ABSTRACT

A magnetic flux leakage inspection method generates a magnetic flux parallel to a surface of an inspected object, and detects a magnetic flux that leaks from the surface of the inspected object with a magnetic sensor. The method includes exciting coils that generate an alternating magnetic field having a variable frequency, an exciting coil power source, a magnetic sensor, a lock-in detector, and a signal analyzer that analyzes changes of a signal intensity and a phase of the output of the magnetic sensor with output signals of the lock-in detector. The method obtains cosine or sine as a trigonometric function of a phase obtained by adding to the phase at each measurement point of multipoint measurement, an adjustment phase common to all the measurement points, and displays an analytical value obtained by multiplying the signal intensity and the sine or cosine at each measurement point with any adjustment phase.

10 Claims, 5 Drawing Sheets

(56) References Cited

U.S. PATENT DOCUMENTS

2006/0247868 A1* 11/2006 Brandstrom .................. 702/35
2008/0211492 A1* 9/2008 Tsukada et al. .............. 324/234
2009/0132181 A1* 5/2009 Girndt ............................ 702/39

FOREIGN PATENT DOCUMENTS

| | | |
|---|---|---|
| JP | 2006-220526 A | 8/2006 |
| JP | 2007-064628 A | 3/2007 |
| JP | 3987941 B2 | 7/2007 |
| JP | 3987941 B2 | 10/2007 |
| WO | WO 2006/109382 A1 | 10/2006 |

OTHER PUBLICATIONS

Partial English language translation of JP 63-129862 U published Aug. 24, 1988.

K. Kosmas et al., "Non-destructive evaluation of magnetic metallic materials using Hall sensors," Journal of Materials Processing Technology 161, 2005, pp. 359-362.

Yuji Goto, "Defect inspection method using non-linear eddy current analysis," Journal of the Institute of Electrical Engineers of Japan, vol. 127, No. 11, 2007, pp. 727-730.

International Search Report for International Application No. PCT/JP2010/059102, Japanese Patent Office, mailed on Jun. 29, 2010, 2 pages.

* cited by examiner (a)  (b)

Defect position

LEAKAGE MAGNETIC FLUX FLAW INSPECTION METHOD AND DEVICE

TECHNICAL FIELD

The present invention relates to a method and an apparatus for inspecting a defect of an inspected objected by applying an alternating magnetic field to the inspected object and detecting a leakage magnetic flux that leaks from a surface of the inspected object.

BACKGROUND ART

A magnetic flux leakage inspection method using magnetism is one of methods that have been used for inspecting a defect of a steel material. The magnetic flux leakage inspection method magnetizes a measured target by direct or alternating magnetization and detects a magnetic flux that leaks from a surface of the measured target mainly using a search coil as a magnetic sensor. Recently, a magnetic resistor device (MR), a hall device, a magnetic impedance device (MI), and the like have begun to be used as the magnetic sensor. In the magnetic flux leakage inspection method using magnetism, when the steel product as the measured target is magnetized by the direct or alternating magnetization, if the measurement target has a defect on a surface, a leakage magnetic flux leakage is generated on the surface. Thus, the magnetic sensor measures a magnetic field component parallel to a surface of the leakage magnetic flux or a magnetic field component perpendicular to the surface of the leakage magnetic flux. A method of magnetizing the measured target includes the direct magnetization and the alternating magnetization using exciting coils. The direct magnetization can uniformly magnetize a cross section of the measured target and thus is mainly used for detecting a defect inside. The alternating magnetization exerts a frequency-dependent skin effect and thus is mainly used for the inspection near the surface of a material. A magnetic sensor with a sensitivity covering a low frequency wave such as the MR, the hall device, and the MI device allows excitation with the low frequency wave and thus is used for detecting a defect deep inside the measured target. The magnetic flux leakage inspection method is generally included in an eddy-current inspection method. The eddy-current inspection method and the magnetic flux leakage inspection method are inspection methods with the same configuration in which the magnetic field is applied to the measured target and the measurement is performed with the magnetic sensor. An eddy-current inspection method applying a low frequency magnetic field and detecting a magnetic field component parallel to a surface of a sample is described in Japanese Patent No. 3987941 (Patent document 1).

The measured target takes various shapes. For detecting a defect of a cylindrical steel pipe and steel bar, it is a common practice to insert the measured target through an encircling coil to be subjected to the alternating magnetization. To inspect a large steel pipe, tank, and the like, since the surface is approximately flat, it is a common practice to attach the exciting coils to a U-shaped yoke member and bring both end portions of the yoke member in contact with the measured target to perform alternating magnetization on the measured target (see, Non-patent documents 1 and 2).

Multipoint measurement data obtained by measuring the measured target at various positions with such a magnetic flux leakage inspection has conventionally been processed as follows. Specifically, an output from the magnetic sensor is directly used as a signal intensity, and a position and a size of a defect are estimated with reference to a change of the signal intensity at measurement positions. Recently, the output from the magnetic sensor has been detected by a lock-in amplifier in synchronization with the exciting coils to analyze a phase in addition to the signal intensity. Specifically, a change of the phase in addition to the change of the signal intensity at the measurement points are graphed to estimate a position and a size of the defect. For example, Japanese Unexamined Patent Application Publication No. 2007-64628 (Patent document 2) describes an analysis method for identifying a depth and a size of a defect from a graph showing a change of a signal intensity.

RELATED ART DOCUMENTS

Patent Documents

Patent document 1: Japanese Patent No. 3987941
Patent document 2: Japanese Unexamined Patent Application Publication No. 2007-64628

Non-Patent Documents

Non-patent document 1: "Non-destructive evaluation of magnetic metallic materials using Hall sensors." K. Kosmas, Ch. Sargentis, D. Tsamakis, E. Hristoforou, *Journal of Materials Processing Technology*, volume 161 (2005) pp. 359-362

Non-patent document 2: "Defect inspection method using non-linear eddy current analysis" Yuji Goto, *Journal of the Institute of Electrical Engineers of Japan*, volume 127 (2007) pp. 727-730

DISCLOSURE OF THE INVENTION

Problems to be Solved by the Invention

As described above, in the conventional magnetic flux leakage inspection methods, the change of the magnetic field intensity and the change of the phase within a measured range are individually graphed or mapped to detect and display the defect. Unfortunately, in these analytical expressions, if a distance between a measured sample and the exciting coils or the magnetic sensor of the measurement apparatus changes during the scanning for the measurement, the changed portion largely affects the measurement result. Thus, in some cases, the position and the size of the defect are difficult to accurately identify.

Accordingly, an object of the present invention is to provide a method and an apparatus for magnetic flux leakage inspection for measurement and analysis that can accurately capture a true signal due to a defect with a measurement result unaffected by a change of a measurement condition.

Means of Solving the Problems

A magnetic flux leakage inspection method in which:
a magnetic field application unit configured to apply an alternating magnetic field to an inspected object;
at least one sensor configured to detect a leakage magnetic flux that leaks from the inspected object; and
an analyzer configured to analyze changes of a signal and a phase output from the at least one sensor, are used to detect the leakage magnetic flux that leaks from the inspected object to inspect a defect, the method including:
applying the alternating magnetic field in a predetermined magnetic field application direction by the magnetic field application unit so that a magnetic flux parallel to a surface of the inspected object is generated;

detecting an intensity of a magnetic field parallel to the predetermined magnetic field application unit at a plurality of positions on the surface of the inspected object by the at least one sensor;

detecting an output from the at least one sensor as two signals having frequencies same as a frequency of the alternating magnetic field and phases orthogonal to each other, and inputting the two signals to the analyzer; and identifying the defect by calculating data on the intensity of the magnetic field and data on the phase at each of the plurality of positions from the two signals input to the analyzer, obtaining a sine value or a cosine value of data obtained by adding a correction phase for calibration to the phase, obtaining product of the data on the intensity of the magnetic field and the sine value or the cosine value, and using values of the product at the plurality of positions, wherein in the identifying the defect, the correction phase for calibration includes a common adjustment phase commonly added to the phases at the plurality of positions to adjust the phases, and the values of the product at the plurality of positions includes the values of the product at the plurality of positions obtained with the common adjustment phase allowing only a change of the magnetic field due to the defect to be extracted among the values of the product at the plurality of positions obtained by changing the common adjustment phase as desired.

The values of the product may be displayed by a display unit.

A magnetic flux leakage inspection apparatus including:

a magnetic field application unit configured to apply an alternating magnetic field to an inspected object;

at least one sensor configured to detect a leakage magnetic flux that leaks from the inspected object; and an analyzer configured to analyze changes of a signal and a phase output from the at least one sensor, the magnetic flux leakage inspection apparatus detecting the leakage magnetic flux that leaks from the inspected object to inspect a defect, wherein the magnetic flux leakage inspection apparatus further includes a lock-in detector configured to detect an output from the at least one sensor as two signals having frequencies same as a frequency of the alternating magnetic field and phases orthogonal to each other, wherein the magnetic field application unit is configured to apply the alternating magnetic field in a predetermined magnetic field application direction so that a magnetic flux parallel to a surface of the inspected object is generated, wherein the at least one sensor is configured to detect an intensity of a magnetic field parallel to the predetermined magnetic field application direction at a plurality of positions on the surface of the inspected object, wherein the analyzer is configured to calculate data on the intensity of the magnetic field and data on the phase at each of the plurality of positions from the two signals, obtain a sine value or a cosine value of data obtained by adding a correction phase for calibration to the phase, obtain product of the data on the intensity of the magnetic field and the sine value or the cosine value, and identify the defect using values of the product at the plurality of positions, wherein the correction phase for calibration includes a common adjustment phase commonly added to the phases at the plurality of positions, and wherein the values of the product at the plurality of positions includes the values of the product at the plurality of positions obtained with the common adjustment phase allowing only a change in the magnetic field due to the defect to be extracted among the values of the product at the plurality of positions obtained by changing the common adjustment phase as desired.

The magnetic flux leakage inspection may further includes an input unit through which the correction phase for calibration is input.

The magnetic flux leakage inspection apparatus may further include a scanning unit configured to move the at least one sensor in a direction intersecting the application direction of the alternating magnetic field.

The magnetic field application unit may include two magnetic pole portions, and the at least one sensor may include a plurality of the sensors arranged between the two magnetic pole portions.

The two magnetic pole portions may include a pair of exciting coils. Planes respectively defined by the exciting coils may face each other. The inspected object may be able to be inserted through the exciting coils. The plurality of sensors may be arranged in a direction parallel to a center axis of the exciting coils.

Effects of the Invention

According to the present invention, a parallel component of a leakage magnetic flux is detected and thus a change of a magnetic field corresponding to a position of a defect can be obtained. Furthermore, a magnetic field signal of the leakage magnetic flux obtained by a sensor array is divided into two signals of a signal intensity and a phase orthogonal to each other, cosine or sine as a trigonometric function of a phase obtained by adding to a phase at each measurement point of a multipoint measurement at a plurality of positions, an adjustment phase to all the measurement points is obtained, an amount is obtained by multiplying the signal intensity and the trigonometric function, and thus a signal change optimum for detecting the defect can be obtained. Accordingly, a position and a size of the defect can be more accurately identified.

According to the present invention, through displaying the values of the product by the display unit, the optimum signal change can be easily obtained by changing the correction phase as desired. Thus, the position and the size of the defect can be identified more accurately.

According to the present invention, a parallel component of a leakage magnetic flux is detected and thus a change of a magnetic field corresponding to a position of a defect can be obtained. Furthermore, a magnetic field signal obtained by a sensor is divided into a signal intensity and a phase by a lock-in detector, cosine or sine as a trigonometric function of a phase obtained by adding to a phase at each measurement point of a multipoint measurement at a plurality of positions, an adjustment phase to all the measurement points is obtained, and an amount is obtained by multiplying the signal intensity and the trigonometric function, and thus an optimum signal change can be obtained. Accordingly, a position and a size of the defect can be more accurately identified.

According to the present invention, any correction phase can be input.

According to the present invention, a defect can be two-dimensionally detected.

According to the present invention, a plurality of sensors are arranged. Thus, the sensors needs not to be moved between magnetic pole portions during an inspection. Accordingly, the inspection can be performed at once without being affected by a change of a measurement condition.

According to the present invention, planes respectively defined by the pair of exciting coils face each other. Thus, an inspected object can be inserted through the exciting coils and thus, a magnetic flux parallel to the center axis between the pair of exciting coils can be introduced to the inspected object. Such a magnetic flux in good orientation facilitates the detection of a magnetic flux leaked from the surface due to a defect of the inspected object. Moreover, a sensor measures the component in the same direction as the magnetic flux and thus, a change of a leakage magnetic flux due to the defect can be more notably detected. Furthermore, a plurality of sensors are arranged. Thus, the sensors need not to be moved between magnetic pole portions during the inspection. Accordingly, the inspection can be performed at once without being affected by a change of a measurement condition.

Figure 1:
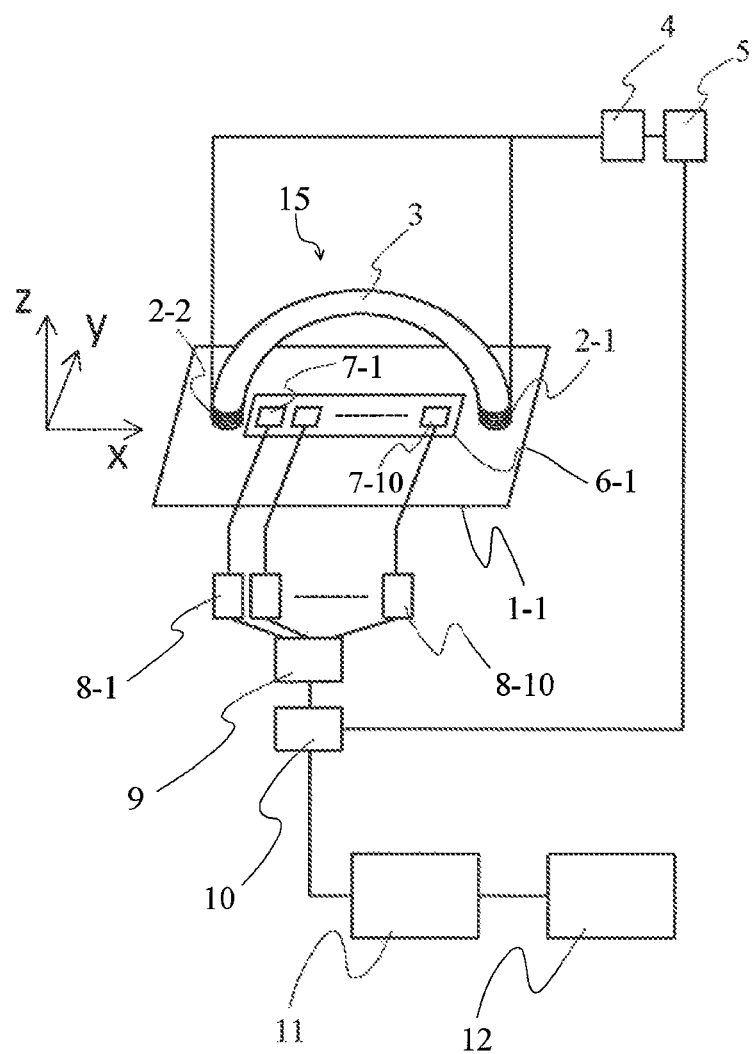
FIG. 1 is a schematic view of a basic configuration of a magnetic flux leakage inspection apparatus employing a magnetic flux leakage inspection method as an embodiment of the present invention.

DESCRIPTION OF THE REFERENCE NUMERAL 1-1 inspected object
1-2 inspected object
1-3 inspected object
2-1 exciting coil
2-2 exciting coil
2-3 exciting coil
2-4 exciting coil
3 yoke member
4 exciting coil power source
5 oscillator
6-1 magnetic sensor array
6-2 magnetic sensor array
6-3 magnetic sensor array
7-1 magnetic sensor
7-2 magnetic sensor
7-3 magnetic sensor
7-4 magnetic sensor
7-5 magnetic sensor
7-6 magnetic sensor
7-7 magnetic sensor
7-8 magnetic sensor
7-9 magnetic sensor
7-10 magnetic sensor
8-1 magnetic sensor measuring circuit
8-2 magnetic sensor measuring circuit
8-3 magnetic sensor measuring circuit
8-4 magnetic sensor measuring circuit
8-5 magnetic sensor measuring circuit
8-6 magnetic sensor measuring circuit
8-7 magnetic sensor measuring circuit
8-8 magnetic sensor measuring circuit
8-9 magnetic sensor measuring circuit
8-10 magnetic sensor measuring circuit
9 multiplexer
10 lock-in detector
11 signal analyzer
12 display mechanism
13 rectangular exciting coil
14 exciting coil base member
15 magnetic field application unit
25 magnetic field application unit

MODES FOR CARRYING OUT THE INVENTION

Embodiments of the present invention are described in detail below with reference to the accompanying drawings.

Members having the same purposes and functions are given the same reference numeral and the description thereof is omitted.

First Embodiment

FIG. 1 is a schematic diagram showing a basic configuration of a magnetic flux leakage inspection apparatus employing a magnetic flux leakage inspection method as an embodiment of the present invention.

The magnetic flux leakage inspection apparatus is an apparatus that detects a leakage magnetic flux that leaks from an inspected object 1-1 to inspect a defect. As shown in FIG. 1, the magnetic flux leakage inspection apparatus mainly includes a magnetic field application unit 15, a magnetic sensor array 6-1, a lock-in detector 10, a signal analyzer 11, and a display mechanism 12.

The magnetic field application unit 15 is a magnetic field application unit that applies an alternating magnetic field to the inspected object 1-1 having a predetermined thickness and includes a pair of exciting coils 2-1 and 2-2, a yoke member 3, an exciting coil power source 4, and an oscillator 5. The exciting coils 2-1 and 2-2 are examples of magnetic pole portions and are respectively wound around both end portions of the U-shaped yoke member 3 in directions opposite to each other. The exciting coils 2-1 and 2-2 are each coupled to the exciting coil power source 4. The oscillator 5 is coupled to the exciting coil power source 4. The magnetic field application unit 15 supplies alternate current to the exciting coils 2-1 and 2-2 so that the exciting coils 2-1 and 2-2 are excited and thus can generate a magnetic flux parallel to a surface of the inspected object 1-1 when the exciting coils 2-1 and 2-2 are in contact with the surface of the inspected object 1-1. Specifically, the magnetic field application unit 15 applies the alternating magnetic field in a predetermined magnetic field application direction (a direction parallel to a straight line between the exciting coils 2-1 and 2-2 in this embodiment) so that the magnetic flux parallel to the surface of the inspected object can be generated.

The shape of the yoke member 3 is not limited to the round U-shape and may be a rectangular U shape.

The magnetic sensor array 6-1 is a sensor that detects a leakage magnetic flux that leaks from the inspected object 1-1 and is an array sensor in which a plurality of magnetic sensors 7-1 to 7-10 are arranged in a longitudinal direction of the magnetic sensor array 6-1. The magnetic sensor array 6-1 is placed on the surface of the inspected object 1-1 with the magnetic sensors 7-1 to 7-10 arranged parallel to the straight line between the exciting coils 2-1 and 2-2. The magnetic sensors 7-1 to 7-10 can detect magnetic field components in a direction parallel to the magnetic field application direction (direction in parallel to the straight line between the exciting coils 2-1 and 2-2) of the magnetic field application unit 15 at a plurality of positions on the surface of the inspected object 1-1. Thus, the magnetic sensor array 6-1 can measure the intensity of the magnetic field in the direction parallel to the magnetic field application direction of the magnetic field application unit 15 in the longitudinal direction of the magnetic sensor array 6-1 at a plurality of points on the surface of the inspected object 1-1. The plurality of magnetic sensors 7-1 to 7-10 are respectively coupled to corresponding magnetic sensor measuring circuits 8-1 to 8-10. The magnetic sensor measuring circuits 8-1 to 8-10 respectively drive the corresponding magnetic sensors 7-1 to 7-10. The magnetic sensor measuring circuits 8-1 to 8-10 are coupled to a multiplexer 9.

The lock-in detector 10 is a lock-in detection unit that detects an output signal from the magnetic sensor array 6-1 as two signals having frequencies same as the alternating magnetic field and phases orthogonal to each other. The lock-in detector 10 only detects a signal in synchronization with an alternate frequency of the alternate current flowing through the exciting coils 2-1 and 2-2. Specifically, the lock-in detector 10 detects the output signal as the two signals having the same frequencies with the exciting coils 2-1 and 2-2 and phases different from each other by 90 degrees. The lock-in detector 10 is coupled to the multiplexer 9.

The signal analyzer 11 is a unit that analyzes changes of the signal and the phase output through the lock-in detector 10 and is coupled to the lock-in detector 10. Specifically, the signal analyzer 11 calculates data on a magnetic field intensity and data on a phase at a plurality of positions from the two signals detected by the lock-in detector 10, obtains a sine value or a cosine value of data obtained by adding a correction phase for calibration to the phase, obtains product of the data on the intensity of the magnetic field and the sine value or the cosine value, and thus can identify the defect using values of the product at the plurality of positions. Thus, the signal analyzer 11 can analyze the signals detected by the lock-in detector 10 with a predetermined analysis method. The display mechanism 12 is coupled to the signal analyzer 11.

The signal analyzer 11 is coupled to an input unit (not shown) through which the correction phase for calibration is input.

The correction phase for calibration (hereinafter, referred to as common adjustment phase a) is a phase for phase adjustment commonly applied to all of the plurality of magnetic sensors 7-1 to 7-10 of the magnetic sensor array 6-1 for calibrating the magnetic sensor array 6-1.

The display mechanism 12 is a display unit that displays an analysis result of the signal analyzer 11. For example, the display mechanism 12 can display information required for identifying the defect on the surface of the inspected object 1-1 such as the changes of the signal and the phase output through the lock-in detector 10 and the value of the product of the data on the intensity of the magnetic field and the sine value or the cosine value.

The magnetic flux leakage inspection method according to this embodiment employed by the magnetic flux leakage inspection apparatus is a magnetic flux leakage inspection method that uses the magnetic flux leakage inspection apparatus to detect the leakage magnetic flux that leaks from the inspected object 1-1 to inspect the defect, the method includes;

applying the alternating magnetic field in the predetermined magnetic field application direction by the magnetic field application unit 15 to generate the magnetic flux parallel to the surface of the inspected object 1-1;

detecting the signal intensity of the magnetic field parallel to the predetermined magnetic field application direction at a plurality of positions on the surface of the inspected object 1-1 by the magnetic sensor array 6-1;

detecting an output from the magnetic sensor array 6-1 as two signals having frequencies same as a frequency of the alternating magnetic field and phases orthogonal to each other, and inputting the two signals to the signal analyzer 11; and identifying the defect by calculating the data on the intensity of the magnetic field and the data on the phase at each of the plurality of positions from the two signals input to the signal analyzer 11, obtaining the sine value or the cosine value of the data obtained by adding the common adjustment phase to the phase, obtaining product of the data on the intensity of the magnetic field and the sine value or the cosine value, and using the values of the product at the plurality of positions.

The magnetic flux leakage inspection apparatus and the magnetic flux leakage inspection method are concretely described below.

As shown in FIG. 1, the alternating magnetic field is applied in a predetermined application direction (direction parallel to the straight line between the exciting coils 2-1 and 2-2) by the exciting coils 2-1 and 2-2 in contact with the surface of the inspected object 1-1. Thus, the magnetic flux parallel to the surface of the inspected object 1-1 is introduced. The pair of exciting coils 2-1 and 2-2 are respectively attached to both ends of the U-shaped yoke member 3. The magnetic flux can be introduced in a direction parallel to a straight line between the ends. The exciting coil power source 4 can change an excitation frequency with the oscillator 5. A signal from the oscillator 5 drives the exciting coil power source 4 so that the alternate current flows through the exciting coils 2-1 and 2-2. The exciting coils 2-1 and 2-2 are wound in directions opposite to each other. One of the exciting coils 2-1 and 2-2 serves as the N-pole for the inspected object 1-1 and the other one of the exciting coils 2-1 and 2-2 serves as the S-pole for the inspected object 1-1. If the inspected object 1-1 has a defect on a front surface, inside, or on a rear surface, a leakage magnetic flux leaks right above the defect and changes the magnetic field. The change is measured at multiple points by the magnetic sensor array 6-1. The magnetic sensors 7-1 to 7-10 of the magnetic sensor array 6-1 are arranged in a facing direction between the exciting coils 2-1 and 2-2, that is, in an x direction in which the magnetic flux is introduced. Each of the magnetic sensors 7-1 to 7-10 of the magnetic sensor array 6-1 detects a magnetic flux density component Bx of the leakage magnetic flux in the longitudinal direction of the magnetic sensor array 6-1, that is, the direction in which the magnetic flux is introduced. A magnetic resistance device (MR) is used as the magnetic sensor for measuring the magnetic flux density component Bx. It is a matter of course that other magnetic sensors such as a magnetic impedance device (MI), a hall device, a flux gate, and a superconductive quantum interference device may be used.

In the magnetic sensor array 6-1, 10 magnetic sensors 7-1 to 7-10 are arranged. It is a matter of course that measurement with higher spatial resolution is possible with a larger number of magnetic sensors and smaller distances among the magnetic sensors. Arranging the plurality of magnetic sensors 7-1 to 7-10 eliminates the necessity of movement (scanning) between the exciting coils 2-1 and 2-2 during the inspection. Thus, the inspection can be performed at once without being affected by the change of a measurement condition. The magnetic sensors 7-1 to 7-10 are respectively provided with the magnetic sensor measuring circuits 8-1 to 8-10 for measurement. Outputs of the magnetic sensor measuring circuits 8-1 to 8-10 are switched by the multiplexer 9 to be detected by the lock-in detector 10. The detection allows detection of only a signal in synchronization with the oscillator 5 generating the signal for the alternate current that flows through the exciting coils 2-1 and 2-2. The signal in-phase with the signal of the oscillator 5 and the signal with a phase shifted by 90 degrees from the phase of the signal of the oscillator 5 are detected by the lock-in detector 10 as two separate signals. With this in-phase signal and this orthogonal signal, a signal intensity Bxi and a phase $\theta i$ of a signal from each of the magnetic sensors 7-1 to 7-10 of the magnetic sensor array 6-1 can be calculated. The signal analyzer 11 calculates Bxi·SIN($\theta i+\alpha$) and the display mechanism 12 displays the data. Here, the analysis proceeds with reference to this data and the common adjustment phase $\alpha$ is changed to obtain an optimum final display. Specifically, through the process of obtaining the optimum final display allows an optimum signal change to be easily obtained by changing the common adjustment phase $\alpha$ as desired. Thus, the position and the size of the defect can be identified more accurately.

As a method of obtaining Bxi·SIN($\theta i+\alpha$) optimum for detecting the position and the size of the defect by changing the common adjustment phase $\alpha$, a predetermined threshold value may be preset as Bxi·SIN($\theta i+\alpha$) and the optimum Bxi·SIN($\theta i+\alpha$) may be automatically obtained by a not shown processing unit of the signal analyzer 11 executing a predetermined program.

Figure 2:
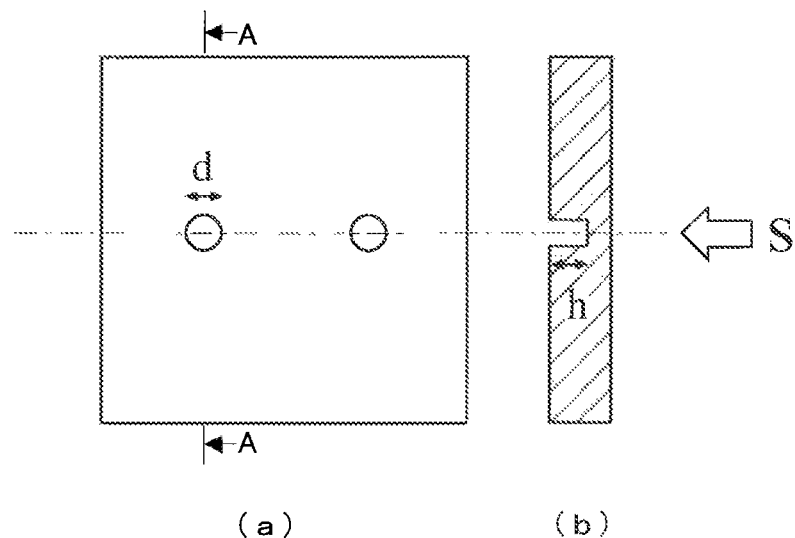
FIG. 2 is a schematic view of a configuration of an inspected object in which (a) is a rear surface view of the inspected object and (b) is a cross-sectional view taken along A-A in (a).

To demonstrate a basic performance of the magnetic flux leakage inspection device, detection of defects is performed on an iron plate with a rear surface shown in FIGS. 2(a) and (b) including two holes having the same shape as the inspected object 1-1. The iron plate has a thickness of 10 mm and a size of 500 mm×500 mm. The holes with a shape of $\phi$30 mm (d shown in FIG. 2(a)) and 6 mm in depth (h shown in FIG. 2(b)) are formed on the rear surface (bottom surface). The holes cannot be seen from the front surface. The holes are measured from the front surface (side pointed by an arrow S) of the inspected object 1-1 using the magnetic flux leakage inspection apparatus shown in FIG. 1 employing the magnetic flux leakage inspection method. Here, 10 magnetic sensors are disposed in the magnetic sensor array 6-1. Accordingly, measurement data at 10 points can be obtained at once. By performing the measurement with the magnetic sensor array 6-1 moved in a predetermined direction, measurement data on a larger area can be obtained from combination of data.

Figure 3:
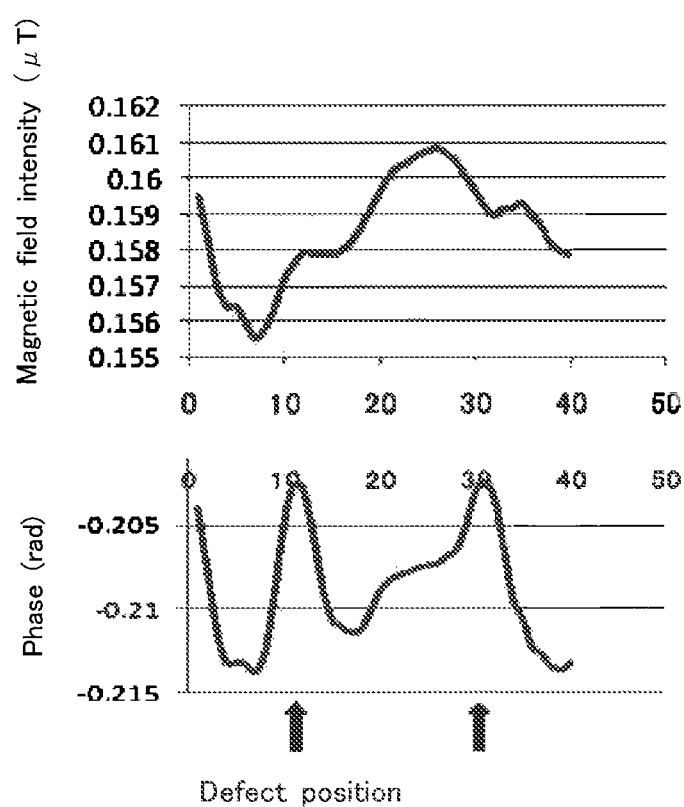
FIG. 3 shows a result of measuring the inspected object and shows a change of a magnetic field intensity (Bxi) and a change of a phase θi at each point i.
Figure 4:
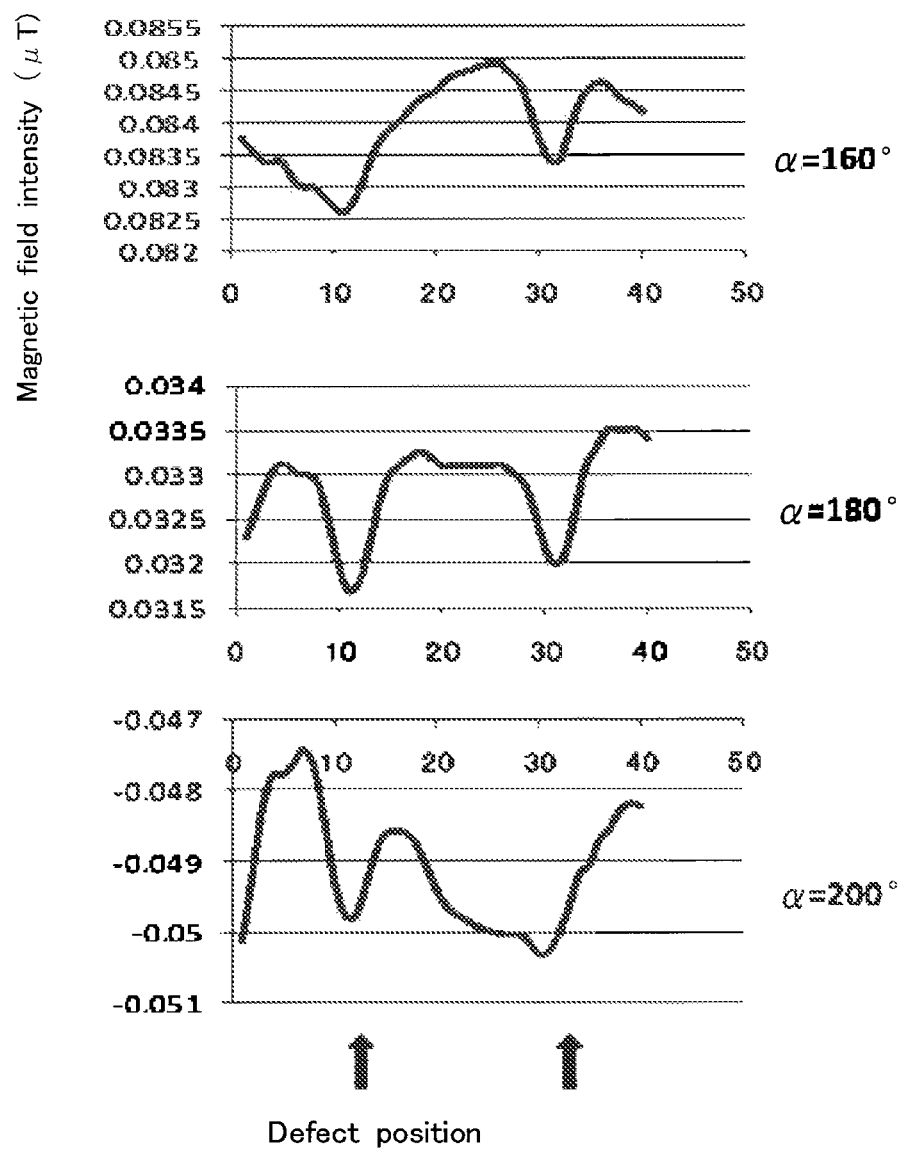
FIG. 4 shows results of measurement on the inspected object and shows the results obtained by obtaining Bxi·SIN (θi+α) at each point i and changing a common adjustment phase α by 20 degrees for each measurement.

FIG. 3 shows a result of measuring the inspected object 1-1 and shows changes of the magnetic field intensity (Bxi) and the phase Di at points i that are measurement points of the magnetic sensors 7-1 to 7-10. In FIG. 3, a horizontal axis and a vertical axis in an upper graph respectively represents point i and magnetic field intensity ($\mu$T) while a horizontal axis and a vertical axis in a lower graph respectively represent point i and phase (rad). FIG. 4 shows results obtained by analysis with the magnetic flux leakage inspection method of the present invention and shows the results obtained by obtaining the magnetic field intensity Bxi·SIN($\theta i+\alpha$) at each point i and by changing the common adjustment phase by a 20 degrees. Conventionally, a defect is detected by referring to a change of a magnetic field intensity and a change of a phase individually as in FIG. 3. In contrast, in the present invention, the magnetic field intensity information and the phase information are combined as in FIG. 4, and the common adjustment phase $\alpha$ is adjusted. Thus, only the change in the magnetic field due to the defect can be notably extracted. In FIG. 4, clear signal changes (two downward peaks) corresponding to positions of the defects can be found with the common adjustment phase $\alpha$ of 180 degrees. Once determined, this common adjustment phase $\alpha$ needs not be adjusted for each measurement, and instead the magnetic flux leakage inspection apparatus is calibrated with a standard sample without a defect and the like.

As the common adjustment phase $\alpha$, any value can be inputted to the signal analyzer 11 through the not shown input unit of the leakage magnetic flux inspection device.

Figure 5:
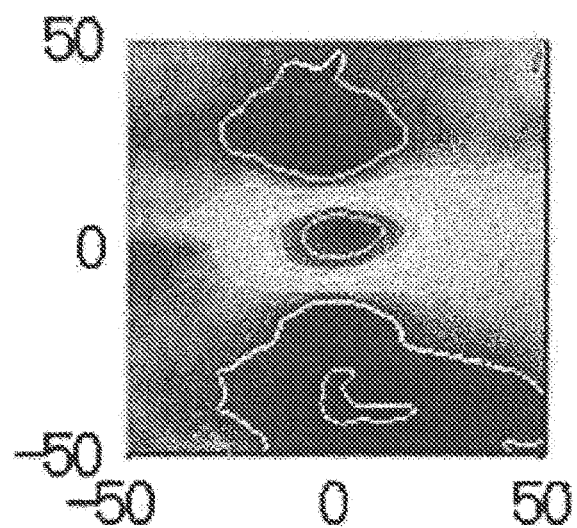
FIG. 5 shows an image obtained from two-dimensional data of Bxi·SIN(θi+α) obtained by two-dimensional scanning by a magnetic sensor array.

Although not shown in the figure, the above-described magnetic flux leakage inspection apparatus may include a scanning unit that moves the magnetic sensor array 6-1 in a direction intersecting the application direction of the alternating magnetic field. Thus, measurement is performed through scanning in a direction perpendicular to the alternating magnetic field application direction that is the longitudinal direction of the magnetic sensor array in this embodiment. Accordingly, two-dimensional data of Bxi·SIN($\theta i+\alpha$) can be obtained and the defect can be detected two dimensionally. As described above, in the magnetic flux leakage inspection apparatus according to this embodiment, a signal most reflecting the defects is obtained when the common adjustment phase is 180 degrees. Thus, the result of the measurement can be displayed as image data with this common adjustment phase. FIG. 5 shows a result of a measurement with a scanning range of 100 mm×100 mm around one of the holes in FIG. 2. Here, an image reflecting the size of the holes is obtained. Thus, the present invention enables the detection of the defect on the rear surface of the inspected object that has been conventionally difficult.

The magnetic field application unit 15 and the magnetic sensor array 6-1 may be integrally formed and provided with the scanning unit so that the magnetic field application unit 15 and the magnetic sensor array 6-1 can integrally move.

By configuring the magnetic flux leakage inspection apparatus and the magnetic flux leakage inspection method employed in the magnetic flux leakage inspection apparatus as described above, the parallel component of the leakage magnetic flux is detected and thus, the change of the magnetic field corresponding to the position of the defect can be captured. Furthermore, the magnetic field signal due to the magnetic flux leakage obtained by the magnetic sensor array 6-1 is divided into two signals of a signal intensity and a phase orthogonal to each other, cosine or sine as a trigonometric function of a phase obtained by adding to a phase at each measurement point of a multipoint measurement at a plurality of positions, the common adjustment phase $\alpha$ common to all the measurement points is obtained, and an amount is obtained by multiplying the signal intensity and the trigonometric function. Thus, the signal change optimum that facilitates the detection of the defect can be obtained. Accordingly, the position and the size of the defect can be more accurately identified.

Moreover, by configuring the magnetic flux leakage inspection apparatus and the magnetic flux leakage inspection method employed in the magnetic flux leakage inspection apparatus as in this embodiment, the pair of exciting coils 2-1 and 2-2 are respectively provided to both ends of the round U or rectangular U-shaped yoke member 3. Thus, the magnetic flux parallel to the straight line between the pair exciting coils 2-1 and 2-2 can be introduced to the inspected object 1-1. Such a magnetic flux in good orientation facilitates the detection of the magnetic flux leaked on the surface due to the defect of the inspected object 1-1. Furthermore, the magnetic sensors measure the components in the same direction as the magnetic flux and thus, the change in the leakage magnetic flux due to the defect can be more notably detected. Furthermore, the plurality of magnetic sensors 7-1 to 7-10 are arranged and thus, the inspection can be performed at once without moving the sensors during the inspection.

Second Embodiment

Next, another embodiment of the magnetic flux leakage inspection apparatus employing the magnetic flux leakage inspection method according to the present invention is described with reference to FIG. 6.

The magnetic flux leakage inspection apparatus according to this embodiment is an apparatus that detects a leakage magnetic flux that leaks from an inspected object 1-2 to inspect a defect. As shown in FIG. 6, the magnetic flux leakage inspection apparatus mainly includes a magnetic field application unit 25, a magnetic sensor array 6-2, as well as the lock-in detector 10, the signal analyzer 11, and the display mechanism 12 shown in FIG. 1. The magnetic sensor array 6-2, the lock-in detector 10, the signal analyzer 11, and the display mechanism 12 are same as those in the first embodiment and detail description thereof will be omitted.

The magnetic field application unit 25 is a magnetic field application unit that applies an alternating magnetic field to the cylindrical inspected object 1-2 (e.g., a steel pipe) having a predetermined thickness. The magnetic field application unit 25 includes a pair of exciting coils 2-3 and 2-4, the exciting coil power source 4, and the oscillator 5. The exciting coils 2-3 and 2-4 are examples of magnetic pole portions. The inspected object 1-2 can be disposed through the exciting coils 2-3 and 2-4 having planes facing each other. The exciting coils 2-3 and 2-4 are wound in directions opposite to each other. The exciting coils 2-3 and 2-4 are each coupled to the exciting coil power source 4. The oscillator 5 is coupled to the exciting coil power source 4. The magnetic field application unit 25 supplies alternate current to the exciting coils 2-3 and 2-4 with the exciting coil power source 4 so that the exciting coils 2-3 and 2-4 are excited and can generate a magnetic flux parallel to (in the x direction in FIG. 6) a surface of the inspected object 1-2 when the inspected objet 1-2 is disposed through the exciting coils 2-3 and 2-4.

The magnetic sensor array 6-2 is a sensor that detects a leakage magnetic flux that leaks from the inspected object 1-2 and is an array sensor in which the plurality of magnetic sensors 7-1 to 7-10 are arranged in a longitudinal direction of the magnetic sensor array 6-2. The magnetic sensor array 6-1 is placed on the surface of the inspected object 1-2 with the magnetic sensors 7-1 to 7-10 arranged in a direction parallel to the center axis of the exciting coils 2-3 and 2-4. The magnetic sensors 7-1 to 7-10 can detect magnetic field components in a direction parallel to the magnetic field application direction (direction in parallel to the center axis of the exciting coils 2-3 and 2-4: x direction) of the magnetic field application unit 15 at a plurality of positions on the surface of the inspected object 1-2. Specifically, the magnetic sensor array 6-2 can measure the intensity of the magnetic field in a direction parallel to the magnetic field application direction of the magnetic field application unit 25 in the longitudinal direction of the magnetic sensor array 6-2 on the surface of the inspected object 1-2 at multiple points. The plurality of magnetic sensors 7-1 to 7-10 are respectively coupled to the corresponding magnetic sensor measuring circuits 8-1 to 8-10. The magnetic sensor measuring circuits 8-1 to 8-10 respectively drive the magnetic sensors 7-1 to 7-10 and are coupled to the multiplexer 9.

The wound shape of the exciting coils 2-3 and 2-4 is not specifically limited to a circular shape in a front view as in this embodiment and may be of a shape suitably corresponding to a tubular inspected object such as an ellipsoidal and a rectangular shape.

Specifically, in this embodiment, the planes respectively defined by the pair of circular exciting coils 2-3 and 2-4 face each other, the inspected object 1-2 that is the cylindrical pipe is inserted through the exciting coils 2-3 and 2-4, and the magnetic flux parallel to the center axis of the steel pipe is introduced. This embodiment uses the magnetic sensor array 6-2 in which the magnetic sensors 7-1 to 7-10 that detect the magnetic field components in the direction parallel to the center axis of the inspected object 1-2 are arranged in the direction parallel to the center axis of the inspected object 1-2. This configuration allows the detection of the defect not only on the surface of the cylindrical measured object but also inside or on an inner surface of the measured object.

By configuring the leakage magnetic flux inspection device as in this embodiment, that is, by arranging the pair of exciting coils 2-3 and 2-4 with the planes facing each other, the inspected object 1-2 can be inserted through the exciting coils 2-3 and 2-4 and the magnetic flux parallel to the center axis between the pair of exciting coils 2-3 and 2-4 can be introduced to the inspected object 1-2. Such a magnetic flux in good orientation facilitates the detection of the magnetic flux leaked on the surface due to the defect of the inspected object. Furthermore, the magnetic sensors measure the components in the same direction as the magnetic flux, the change in the magnetic flux leakage due to the defect can be more notably detected. Furthermore, the plurality of magnetic sensors 7-1 to 7-10 are arrange and thus, the inspection can be performed at once without moving the sensors during the inspection.

Third Embodiment

Figure 7:
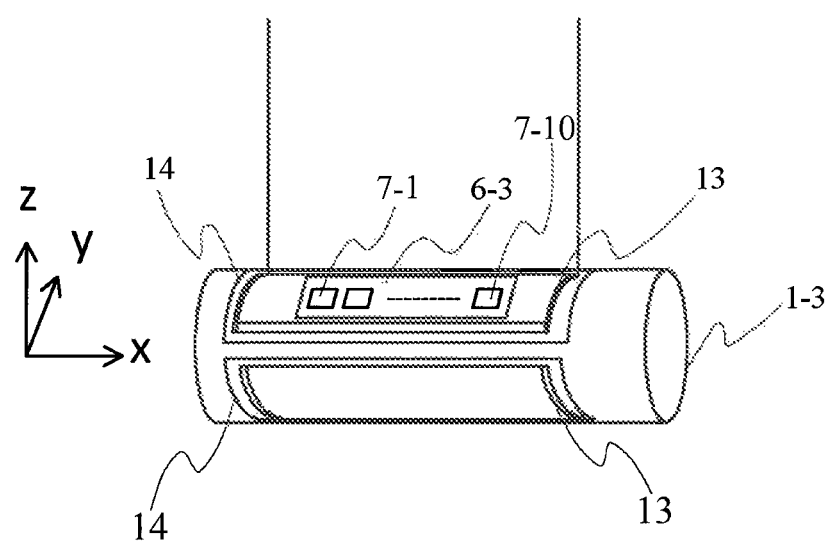
FIG. 7 is a schematic diagram showing a basic configuration of a magnetic flux leakage inspection device as a third embodiment of the present invention.

Next, still another embodiment of the magnetic flux leakage inspection apparatus employing the magnetic flux leakage inspection method according to the present invention is described by referring to FIG. 7.

Figure 6:
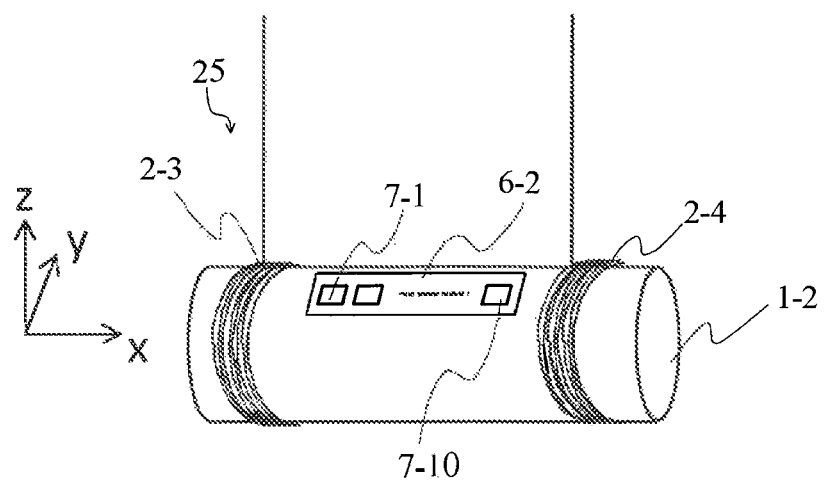
FIG. 6 is a schematic view a basic configuration of a magnetic flux leakage inspection device as a second embodiment of the preset invention.

FIG. 7 shows another mode for providing the same function of the embodiment in FIG. 6 of the present invention. In FIG. 6, to measure the cylindrical steel pipe, the exciting coils 2-3 and 2-4 are wound around the cylinders. However, if the steel pipe has a large diameter, the exciting coil may be difficult to wound. As a method to address this, an exciting coil that applies a magnetic field to an inspected object 1-3 can be formed by combining multiple rectangular exciting coils 13 each having a predetermined size to wrap around the inspected objected 1-3 (steel pipe) as shown in FIG. 7. Specifically, each of the rectangular exciting coils 13 is formed on a flexible exciting coil base member 14 and thus can snugly fit to the cylindrical shape and can be adhered on a surface of the cylindrical steel pipe as the inspected object 1-3. By serially coupling the rectangular exciting coils 13 in the circumferential direction of the inspected object 1-3, the function approximately the same with that of the circular exciting coils 2-3 and 2-4 in FIG. 6 can be provided. A wiring part of the exciting coil disposed along the longitudinal direction of the cylinder overlaps with the wiring of the adjacent exciting coil 13.

Thus, the current flowing through the exciting coil 13 and the current flowing through the adjacent exciting coil 13 flow in directions opposite to each other and thus cancel each other out. On the other hand, a wiring part in the circumference direction of the exciting coil 13 does not overlap with the wiring part of the adjacent exciting coil 13. Thus, in this wiring part, the current flowing through the exciting coil 13 is in the direction same as the current flowing through the adjacent exciting coil 13. As a result, current can flow through the entire circumference of the cylindrical steel pipe. Thus, the magnetic field application unit of this embodiment can provide approximately the same function as the exciting coils 2-3 and 2-4 in FIG. 6. Furthermore, the coils can be separately attached, and thus the exciting coil that can be very easily detached can be realized. The leakage magnetic flux is measured using the magnetic sensor array 6-3 in which the plurality of magnetic sensors 7-1 to 7-10 that detects the magnetic field components in the direction (x direction) parallel to the center axis of the exciting coils are arranged as in the embodiment in FIG. 6.

As described above, the magnetic flux leakage inspection apparatus employing the magnetic flux leakage inspection method is an apparatus that generates a magnetic flux parallel to a surface of an inspected object, and detects a magnetic flux that leaks from the surface of the inspected object with a magnetic sensor. The magnetic flux leakage inspection apparatus includes exciting coils that generate an alternating magnetic field having a variable frequency, an exciting coil power source, the magnetic sensor that detects a component horizontal to a magnetic field leaked from the surface of the inspected object, a lock-in detector that detects signals having the same frequency as the exciting coils from an output from the measuring circuit of the magnetic sensor, and a signal analyzer that analyzes changes of a signal intensity and a phase of the output of the magnetic sensor with output signals of the lock-in detector. The magnetic flux leakage inspection apparatus obtains cosine or sine as a trigonometric function of a phase obtained by adding to the phase at each measurement point of multipoint measurement, an adjustment phase common to all the measurement points, and displays an analytical value obtained by multiplying the signal intensity and the sine or the cosine at each measurement point with any adjustment phase.

Furthermore, in the magnetic flux leakage inspection apparatus employing the magnetic leakage inspection method according to the present invention, a parallel component of a leakage magnetic flux is detected and thus, a change of a magnetic field corresponding to a position of a defect can be captured. Furthermore, a magnetic field signal is divided into a signal intensity and a phase, cosine or sine as a trigonometric function of a phase obtained by adding to the phase at each measurement point of multipoint measurement, an adjustment phase common to all the measurement points is obtained, and an amount is obtained by multiplying the signal intensity by the trigonometric function. Thus, a signal change optimum for detecting the defect can be obtained. Accordingly, a position and a size of the defect can be more accurately identified.

The present invention is not limited to the above-described embodiments and it is a matter of course that various modifications, design variations and the like without departing from the technical idea of the present invention are included in the technical scope of the present invention.

INDUSTRIAL APPLICABILITY

The present invention is a magnetic flux leakage inspection method that applies an alternating magnetic field to a measured target of a steel structure to detect a defect on a front surface, inside, or on a rear surface side. While a conventional magnetic flux leakage inspection method detects a defect on the front surface with a high accuracy, the present invention allows a detection of a defect at a deeper portion or on a rear surface side. Thus, the present invention can be applied to defect detection for an internal defect of a tank and a pipe in an industrial plant as well as defect detection for a welded portion of a bridge and the like.

The invention claimed is:

1. A magnetic flux leakage inspection method comprising:
applying an alternating magnetic field in a predetermined magnetic field application direction with a magnetic field application unit so that a magnetic flux parallel to a surface of an inspected object is generated;
detecting an intensity of a magnetic field parallel to the predetermined magnetic field application direction at a plurality of positions on the surface of the inspected object by at least one sensor configured to detect a leakage magnetic flux that leaks from the inspected object;
detecting an output from the at least one sensor as two signals having frequencies the same as a frequency of the alternating magnetic field and phases orthogonal to each other;
inputting the two signals to an analyzer configured to analyze changes of the two signals and the phases output from the at least one sensor; and
identifying a defect in the inspected object by calculating data on the intensity of the magnetic field and data on the phase at each of the plurality of positions from the two signals input to the analyzer, obtaining a sine value or a cosine value of the calculated phase data by adding a correction phase for calibration to the phase, obtaining a product of the calculated data on the intensity of the magnetic field and the sine value or the cosine value, and using values of the product at the plurality of positions,
wherein the correction phase for calibration comprises a common adjustment phase commonly added to the phases at the plurality of positions to adjust the phases, and wherein the values of the product at the plurality of positions comprises the values of the product at the plurality of positions obtained with the common adjustment phase allowing only a change of the magnetic field due to the defect to be extracted among the values of the product at the plurality of positions obtained by changing the common adjustment phase as desired.

2. The magnetic flux leakage inspection method according to claim 1 further comprising displaying the values of the product by a display unit.

3. A magnetic flux leakage inspection apparatus comprising:
a magnetic field application unit configured to apply an alternating magnetic field to an inspected object;
at least one sensor configured to detect a leakage magnetic flux that leaks from the inspected object; and
an analyzer configured to analyze changes of a signal and a phase output from the at least one sensor, the magnetic flux leakage inspection apparatus detecting the leakage magnetic flux that leaks from the inspected object to inspect a defect,
wherein the magnetic flux leakage inspection apparatus further comprises a lock-in detector configured to detect an output from the at least one sensor as two signals having frequencies the same as a frequency of the alternating magnetic field and phases orthogonal to each other, wherein the magnetic field application unit is configured to apply the alternating magnetic field in a predetermined magnetic field application direction so that a magnetic flux parallel to a surface of the inspected object is generated, wherein the at least one sensor is configured to detect an intensity of a magnetic field parallel to the predetermined magnetic field application direction at a plurality of positions on the surface of the inspected object, wherein the analyzer is configured to calculate data on the intensity of the magnetic field and data on the phase at each of the plurality of positions from the two signals, obtain a sine value or a cosine value of the calculated phase data by adding a correction phase for calibration to the phase, obtain a product of the calculated data on the intensity of the magnetic field and the sine value or the cosine value, and identify the defect using values of the product at the plurality of positions, wherein the correction phase for calibration comprises a common adjustment phase commonly added to the phases at the plurality of positions, and wherein the values of the product at the plurality of positions comprises the values of the product at the plurality of positions obtained with the common adjustment phase allowing only a change in the magnetic field due to the defect to be extracted among the values of the product at the plurality of positions obtained by changing the common adjustment phase as desired.

4. The magnetic flux leakage inspection apparatus according to claim 3 further comprising an input unit through which the correction phase for calibration is input.

5. The magnetic flux leakage inspection apparatus according to claim 4, further comprising a scanning unit configured to move the at least one sensor in a direction intersecting the application direction of the alternating magnetic field.

6. The magnetic flux leakage inspection apparatus according to claim 4, wherein the magnetic field application unit comprises two magnetic pole portions, and wherein the at least one sensor comprises a plurality of the sensors arranged between the two magnetic pole portions.

7. The magnetic flux leakage inspection apparatus according to claim 3 further comprising a scanning unit configured to move the at least one sensor in a direction intersecting the application direction of the alternating magnetic field.

8. The magnetic flux leakage inspection apparatus according to claim 7, wherein the magnetic field application unit comprises two magnetic pole portions, and wherein the at least one sensor comprises a plurality of the sensors arranged between the two magnetic pole portions.

9. The magnetic flux leakage inspection apparatus according to claim 3, wherein the magnetic field application unit comprises two magnetic pole portions, and wherein the at least one sensor comprises a plurality of the sensors arranged between the two magnetic pole portions.

10. The magnetic flux leakage inspection apparatus according to claim 9, wherein the two magnetic pole portions comprises a pair of exciting coils, wherein planes respectively defined by the exciting coils face each other, wherein the inspected object is able to be inserted through the exciting coils, and wherein the plurality of sensors are arranged in a direction parallel to a center axis of the exciting coils.

* * * * *

UNITED STATES PATENT AND TRADEMARK OFFICE
CERTIFICATE OF CORRECTION

PATENT NO. : 9,146,214 B2
APPLICATION NO. : 13/381347
DATED : September 29, 2015
INVENTOR(S) : Keiji Tsukada It is certified that error appears in the above-identified patent and that said Letters Patent is hereby corrected as shown below:

In the specification

Column 7, line 53, please replace "phase a" with --phase α--.

Column 9, line 20, please replace "a phase □i" with --a phase θi--.

Column 9, line 59, please replace "the phase Di" with --the phase θi--.

Column 9, line 62, please replace "intensity (□T)" with --intensity (μT)--.

Signed and Sealed this
Fifth Day of April, 2016

Michelle K. Lee
*Director of the United States Patent and Trademark Office*